United States Patent [19]

Chubbuck et al.

[11] 4,265,252
[45] May 5, 1981

[54] INTRACRANIAL PRESSURE IMPLANT

[75] Inventors: John G. Chubbuck, Silver Spring; James T. Turner, Ellicott City, both of Md.

[73] Assignee: The Johns Hopkins University, Baltimore, Md.

[21] Appl. No.: 897,716

[22] Filed: Apr. 19, 1978

[51] Int. Cl.³ .............................................. A61B 5/02
[52] U.S. Cl. ..................................... 128/748; 73/718
[58] Field of Search .................. 73/780, 718, 722, 724, 73/728, 725, 729, 706; 128/748

[56] References Cited

U.S. PATENT DOCUMENTS

| | | | |
|---|---|---|---|
| 3,027,769 | 4/1962 | Coon | 73/724 X |
| 3,356,963 | 12/1967 | Buck | 73/718 X |
| 3,405,559 | 10/1968 | Moffatt | 73/724 X |
| 3,422,324 | 1/1969 | Webb | 73/718 X |
| 3,838,684 | 10/1974 | Manvel et al. | 73/724 X |
| 3,958,558 | 5/1976 | Dunphy et al. | 128/2.05 E X |
| 4,026,276 | 5/1977 | Chubbuck | 128/2.05 E X |
| 4,062,354 | 12/1977 | Taylor et al. | 128/2 P X |
| 4,096,758 | 6/1978 | Moore | 73/718 |
| 4,109,535 | 8/1978 | Reed et al. | 73/706 |
| 4,127,110 | 11/1978 | Bullara | 128/2.05 E X |

Primary Examiner—Robert W. Michell
Assistant Examiner—Francis J. Jaworski
Attorney, Agent, or Firm—Robert E. Archibald; Samuel L. Sachs

[57] ABSTRACT

An implantable transensor device containing a passive RF resonant circuit having a natural frequency influenced by the pressure of the sensor's environment in a body cavity of a living entity. The circuit of the transensor includes an inductor and a capacitor, at least one of which varies in value in direct relation to variation of environmental pressure to change the resonant frequency of the circuit. The circuit can be externally interrogated to determine the resonant frequency thereof at any point in time by the imposition thereon of swept frequency electromagnetic radiation provided by a monitoring device which determines when some of the radiation is absorbed as a result of the frequency of the radiation being the same as the resonant frequency of the transensor circuit. An imposed relationship exists between the sensed environmental pressure, and the reactance of the reactive components of the circuit. A natural relationship exists between pressure sensitive reactance, and the resonant frequency of the circuit. As a result, an increase in environmental pressure causes a corresponding increase in frequency and a decrease in environmental pressure causes a decrease in frequency.

18 Claims, 7 Drawing Figures

INTRACRANIAL PRESSURE IMPLANT

STATEMENT OF GOVERNMENT INTEREST

The Government has rights in this invention pursuant to research grant NS-11710 from the Department of Health, Education and Welfare.

BACKGROUND OF THE INVENTION

A. Field of the Invention

The present invention relates to apparatuses for monitoring intracranial pressure in diagnostic and post-operative situations, and more particularly, to an intracranial pressure transensor which is entirely implantable within a living body and which includes a resonant circuit that varies in frequency in a direct relationship with variations in pressure.

B. Description of the Prior Art

The need for monitoring intracranial pressure in patients having certain physiological conditions has been long recognized. These conditions include hydrocephalic conditions, conditions where patients have undergone neurosurgery, and other critical situations where individuals are subject to brain swelling, edema, obstruction of cerebral spinal fluid pathways, or intracranial space occupying lesions. Convenient and accurate monitoring of the intracranial pressure in these situations frequently allows institution of correctional emergency procedures when intracranial pressure rises or falls to dangerous levels.

Present methods for monitoring intracranial pressure include implantation of a pressure transducer which requires a portion thereof, such as a wire or coupling to pass through the skull and scalp of the subject in which the device is implanted. Such a technique is largely unsatisfactory as danger of infection, patient discomfort, reduced patient mobility, and the use of surgical procedures to remove the apparatus when it is no longer needed are inherent.

Intracranial pressure monitoring apparatuses which are entirely implantable and employ variable frequency tuned circuits whose frequencies vary in relation to pressure are also known. These apparatuses mechanically translate a change in pressure into a change in reactance of a reactive component of the L/C circuit employed so that the frequency thereof shifts. This relationship is embodied in apparatuses presently known so that an increase in pressure will cause either an increase in capacitance or inductance in the tuned circuit thereby causing a decrease in the resonant frequency of the circuit. Typical of apparatuses employing such a relationship are those disclosed in U.S. Pat. No. 3,958,558 issued to R. R. Dunphy et al and U.S. Pat. No. 4,026,276 issued to J. G. Chubbuck on May 31, 1977, said latter patent being assigned to the assignee of the present invention. A decrease in frequency as a result of an increase in pressure as monitored by the above-noted intracranial pressure monitors, when the variable reactive component is a capacitor, leads to a situation where greatest read-out sensitivity is at the high end of the pressure range which can be monitored, since that is where a change in pressure produces the greatest change in capacitive reactance and therefore produces greatest frequency shift. However, it is desirable to have maximum sensitivity at pressures closest to normal since this is when corrective action is first indicated.

In addition, presently known apparatuses of the character described above which employ variable capacitors and fixed inductors are disclosed as approaching maximum capacitance as pressure increases. As a result, highly elevated cranial pressures, in certain circumstances, can exceed the maximum limits of the variable capacitor employed, likely leading to shorting of the capacitor and therefore temporary inoperation of the monitoring process. Another feature of presently known intracranial pressure monitors that employ resonant circuits is the relationship between the variable capacitance of the resonant circuit and the stray capacitance substantially attributable to conductive body fluids in which the monitor is implanted. Minimum sensitivity as noted above, as well as maximum frequency shift due to implantation into a conductive fluid is inherent in presently known apparatuses since the ratio of variable capacitance of the resonant circuit to the stray capacitance provided by the conductive body fluids is at a minimum at pressures close to normal.

An additional characteristic of presently known intracranial pressure monitors which employ L/C resonant circuits is difficulty in calibration. Typically, these apparatuses are small in size and tolerances of much less than a thousandth of an inch are not uncommon to insure accurate calibration of the mechanical structures associated with the reactive element of the resonant circuit which varies in response to changes in pressure. Presently known apparatuses rely upon the dimensional stability of the housing which houses the resonant circuit and the reactive component which is varied to insure calibration of that component. As a result, the housing itself, which might be manufactured and assembled to lower tolerances, must be made to conform to otherwise unnecessarily exacting standards. Trying to attain these standards in a housing is difficult and costly.

The present invention provides several significant advances over the prior art by providing an intracranial pressure implant which has its greatest read-out sensitivity at pressure levels closest to normal, which is subject to inconsequential frequency shifts due to implantation, which is not subject to inoperation due to high pressure levels experienced during use, and which insures dimensional stability between the mechanical components of the variable reactive element of the inductor capacitor-resonant circuit employed therein, without reliance upon dimensional stability of the housing which encloses the resonant circuit.

SUMMARY OF THE INVENTION

Therefore, a primary object of the present invention is to provide an apparatus for monitoring intracranial pressure without the need for percutaneous extracranial electrical connections or coupling conduits.

A further object of the present invention is to provide an implantable pressure transensor which passively provides an indication of intracranial pressure to an extracranial monitoring apparatus on interrogation of the transensor.

A still further object of the present invention is to provide an implantable intracranial pressure monitor which is characterized by greatest sensitivity at pressures closest to those normal to the body in which the apparatus is implanted.

Still another object of the present invention is to provide an intracranial pressure implant wherein the frequency shift due to implantation into a conductive fluid is minimized to the point of negligibility.

Still another further object of the present invention is to provide an intracranial pressure implant which is not subject to inoperation at high pressures.

Another further object of the present invention is to provide an intracranial pressure implant which provides for structural stability between the mechanical elements of the reactive element which is varied in response to changes in pressure independent of the dimensional stability of the housing which encapsulates the resonant circuit.

Another still further object of the present invention is to provide an intracranial pressure implant which is simple in design, inexpensive to manufacture, rugged in construction, relatively easy to employ, and efficient in operation.

These objects, as well as further objects and advantages of the present invention will become readily apparent after reading the ensuing description of a non-limiting illustrative embodiment and the accompanying drawings.

An apparatus for sensing pressure within a cavity in the body of a living entity, according to the principles of the present invention, includes an inductor-capacitor resonant circuit means, means responsive to the pressure disposed in the cavity, and means for increasing the resonant frequency of the resonant circuit means in response to an increase in the pressure as sensed by the pressure responsive means and for decreasing the resonant frequency of the resonant circuit means to response to a decrease in the pressure as sensed by the pressure responsive means. Specifically, the present invention provides an intracranial pressure monitor which can be permanently places in a trephine or "burr" hole in the skull and which operates without the need for percutaneous extra-cranial connections to a monitoring apparatus.

BRIEF DESCRIPTION OF THE DRAWINGS

In order that the present invention may be more fully understood it will now be described, by way of example, with reference to the accompanying drawing in which.

DESCRIPTION OF THE PREFERRED EMBODIMENT

Figure 1:
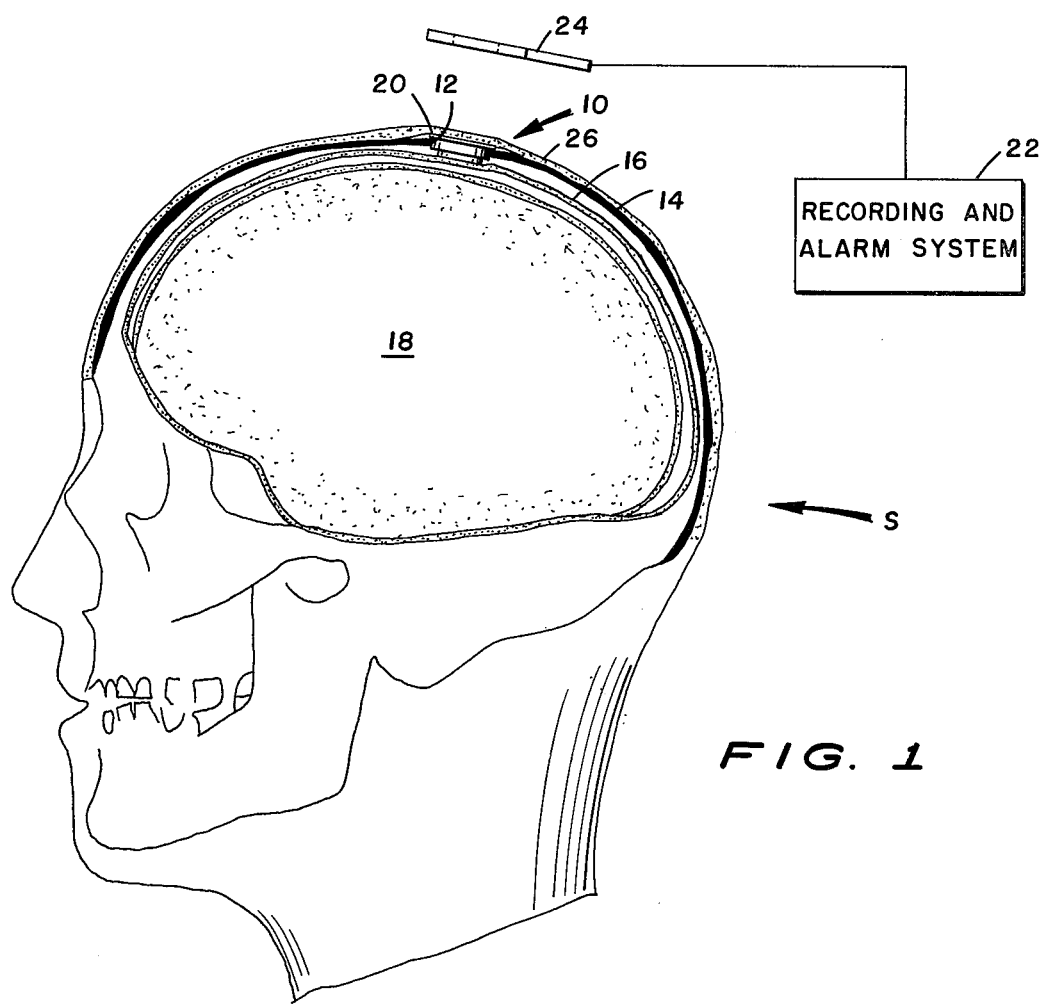
FIG. 1 is a schematic representation illustrating the environment and general operation of the present invention.

Referring now to the Figures, and more particularly to FIG. 1 thereof, there is illustrated therein an intracranial pressure monitoring implant 10 constructed in accordance with the principles of the present invention.

The implant 10 is illustrated positioned within a burr hole 12 in the skull 14 of a subject S whose intracranial pressure must be monitored. The lower face of the implant 10 is positioned against the dura 16, a membrane which lies beneath the skull 14 and above the subcranial space, i.e. the space between the skull and the brain 18. The pressure implant 10 can be mounted by a mounting flange 20 as illustrated and as hereinafter described in conjunction with FIGS. 6 and 7, or the implant 16 may be otherwise retained within the skull 14 so long as the lower surface of the implant 10 bears against the dura 16 without sufficiently deflecting the same downwardly enough so as to obliterate the subarachnoid space below the implant 10. As a result of the positioning of the implant 10, the dura 16 serves to transmit subdural cerebral spinal fluid pressure to the implant 10. This pressure, when sensed by the implant 10, is translated into a frequency shift of a resonant circuit disposed within the implant 10, and which is sensed and measured by an external recording and alarm system 22.

The recording and alarm system 22 provides an inductive probe 24 which is placed adjacent to the scalp 26 of the subject S proximate to the location of the burr hole 12 and therefore the implant 10 when the implant is to be interrogated. The recording and alarm system 22 serves to translate a shift in frequency of the resonant circuit provided by the implant 10 to pressure descriptive data. The system 22 preferably is employed to provide a continuous record of intracranial pressure and may include a visual or audio alarm to alert medical personnel of a dangerously high or low intracranial pressure. An apparatus suitable for employment as a recording and alarm system is disclosed and claimed in U.S. Pat. No. 4,114,606, based upon an application by G. Seylar filed on Nov. 12, 1976, with an assignee common to this application. Upon a careful reading of the ensuing description of the present invention it should be apparent to one skilled in the art that other systems such as a grid dip oscillator may be employed to interrogate the implant 10 of the present invention and to translate the information ascertained by the interrogation into frequency and/or pressure-type data.

Figure 3:
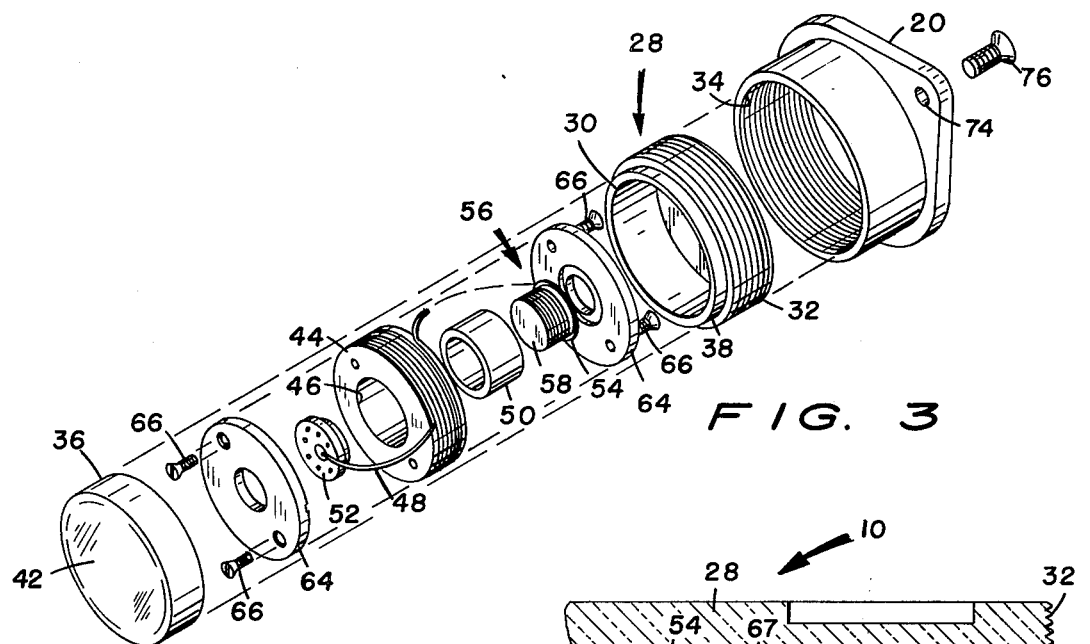
FIG. 3 is an exploded assembly view in perspective of the preferred embodiment of the present invention.

With reference to FIG. 3 there is illustrated therein the components which comprise the intracranial pressure monitoring implant 10 constructed in accordance with the principles of the present invention. These elements are illustrated in preferred and sometimes arbitrary shapes which could be modified by one skilled in the art without departure from the teachings of the present invention. For instance, the implant 10 and the components thereof could take the form of an oblong, square, rectangle, etc. instead of the shape of a circle as illustrated.

Figure 4:
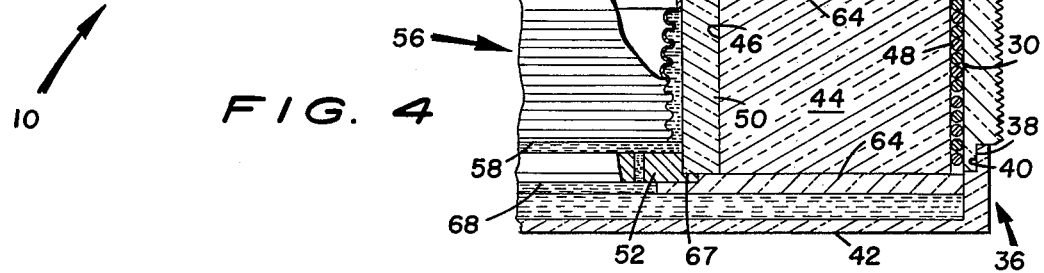
FIG. 4 is a fragmentary cross-sectional view of the preferred embodiment.
Figure 5:
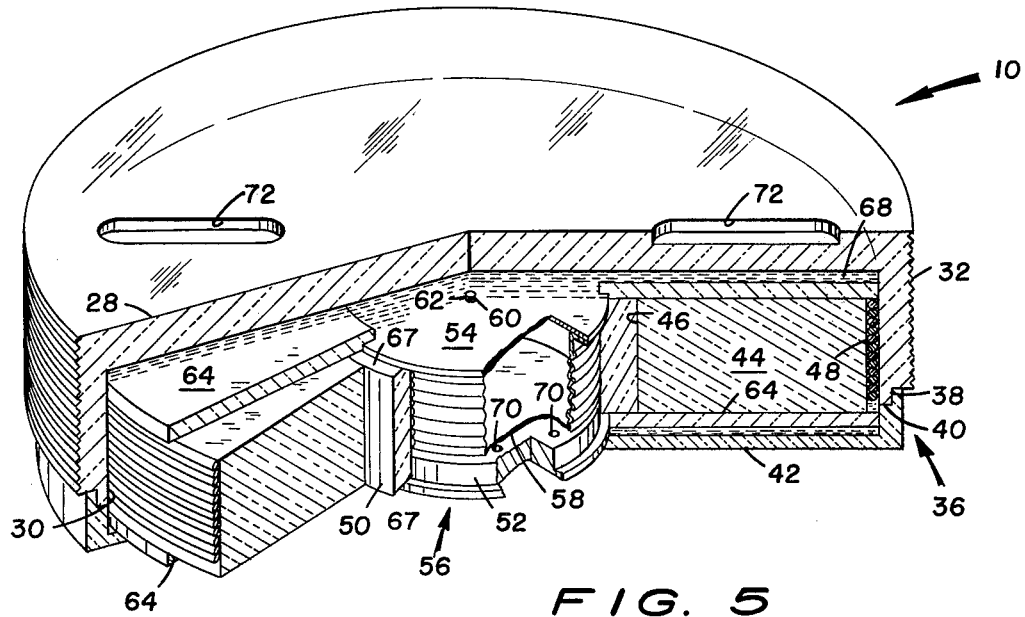
FIG. 5 is a perspective view of the preferred embodiment in partial cross-section.

The implant 10 includes a housing 28 forming a chamber 30 therein. The external edges 32 of the housing 28 are provided with threads which cooperate with internal threads provided on the interior surface 34 of the mounting flange 20 so that the housing 28 can be threadably engaged thereby for implantation. A cover 36 is provided to seal the chamber 30 of the housing 28 from the outside environment subsequent to the assembly of the implant 10. The housing 28 is provided with an undercut annular lip 38 that frictionally engages an internal annular recess 40 provided by the cover 36 when the implant 10 is assembled as illustrated in FIGS. 4 and 5. Other suitable means may be employed to join the cover 36 to the housing 28. Once the annular lip 38 is frictionally engaged by the internal annular recess 40, the housing 28 and the cover 36, which are both preferably constructed of a biocompatible plastic such as Lexan or Polysulfone, are cemented together by a suitable cement. For instance, if the housing 28 and the cover 36 are constructed of Polysufone, a suitable cement can be formed by dissolving a grit of Polysulfone in dichloroethane. The cover 36 is provided with a flexible membrane 42 as one surface thereof. The flexible membrane 42 may be a thin wall section of the cover 36 which is integrally formed therewith or may be a separate component mounted upon the cover as long as the membrane 42 exhibits sufficient elastic compliance such that a perceptible deformation will ensue subsequent to an increase in dura pressure thereagainst.

The heart of the assembly of the implant 10 which is disposed within the chamber 30 of the housing 28 is a coil form 44 of a non-conductive material which has a longitudinal bore 46 disposed therethrough. A suitable length of wire 48 is helically wrapped around the coil form 44 to form an inductor. A rigid spacer 50, the character of which will be hereinafter described, is dimensioned so that it may be received and operably reside within the longitudinal bore 46 of the coil form 44. The rigid spacer 50 is preferably tubular in shape and is constructed of quartz glass or a similar material which can be depended upon to maintain a high degree of dimensional stability. The rigid spacer 50 serves to absolutely fix the distance between the fixed capacitance plate 52 and a flange 54 provided by a bellows 56. The bellows 56 provides a movable surface which serves as a movable capacitance plate 58. Capacitance develops between the movable capacitance plate 58 and the fixed capacitance plate 52 when the bellows 56 and the fixed capacitance plate 52 are assembled and fixedly secured at opposing ends of the rigid spacer 50 as illustrated in FIGS. 4 and 5. The wire 48, which forms an inductor, is connected across the capacitor formed by the bellows 56 and the fixed capacitance plate 52 to form an inductor-capacitor resonant circuit. The bellows 56 is constructed of nickel which is gold plated and the fixed capacitance plate 52 is preferably constructed of brass.

The bellows 45 encloses a quantity of gas, preferably nitrogen, which is under pressure of one atmosphere. The gas is supplied to the bellows 56 through an aperture 60 located in the flange 54 and is sealed therein by a pin 62 soldered in the aperture 60 as illustrated in FIG. 5. The fixed capacitance plate 52 and the flange 54 of the bellows 56 are forced tightly against the contacting edges of the rigid spacer 50 by a pair of clamping plates 64 which sandwich the plate 52, flange 54, and the spacer 50. The clamping plates 64 are affixed to the coil form 44 by a plurality of screw 66, the clamping plates 64 thereby pressuring the fixed capacitance plate 52 and the bellows flange 54 tightly against the rigid spacer 50 as shown in FIGS. 4 and 5.

Considering FIGS. 4 and 5, the intracranial pressure monitoring implant 10 is illustrated in an assembled condition. The bellows flange 54 and the fixed capacitance plate 52 are tightly clamped against the contacting edges 67 of the rigid spacer 50 by the clamping plates 64 which are secured to the coil form 44 by the plurality of screws 66. The clamping plates 64 are provided with annular recesses to accommodate part of the depth of the fixed capacitance plate 52 and the flange 54 so that these components may be registered and aligned. When assembled, the bellows 56 is disposed within the rigid spacer 50 so that the end thereof providing the movable capacitance plate 58 may freely reciprocate therein thereby forming a variable capacitor developing capacitance between the fixed capacitance plate 52 and the movable capacitance plate 58. Since the rigid spacer 50 is dimensionally stable, the calibration of the capacitor formed by the bellows 56 and fixed capacitance plate 52 is entirely independent of the other structures of the implant 10 including the housing 28. Therefore, the variable capacitor can be preassembled and accurately calibrated by precise grinding of the rigid spacer 50. This calibration will not be disturbed by assembly of the implant 10. by shock to the housing 28, or by dimensional instability of other components of the implant 10.

The chamber 30 formed by the housing 28 is filled with a suitable fluid 68, such as medical grade silicon liquid, which is chosen for its low ability to absorb moisture, its non-toxic characteristics, and its low dielectric constant which serves to minimize stray capacitance. The fluid 68 serves to translate inward deformation of the flexible membrane 42 into compression of the bellows 56. Since the housing 28 and the cover 36 are constructed of a rigid material with the exception of the flexible membrane 42, pressure upon the flexible membrane 42 will seek to compress the fluid 68. However, since the fluid 68 is relatively incompressible it will act upon anything within the chamber 30 that is compressible, i.e., the bellows. The fluid 68 flows freely around the exterior of the bellows 56 since a plurality of apertures 70 permit free passage of the fluid therethrough. As body cavity pressure is transmitted to the fluid 68, the bellows 56 is compressed by the pressure acting against the reference gas pressure of nitrogen which is disposed therein. Although nitrogen is suggested because of its non-toxic properties, a given mass of another gas or other compressible fluid may be employed as long as condensable gases such as water vapor are removed therefrom. It is also important to note that the diffusion rate of the gas through the bellows 56 must approach zero as closely as practicable and therefore a bellows constructed of metal as hereinbefore described is indicated. The housing 28 is preferably provided with a pair of notches 72 that can be engaged by a suitable tool to facilitate threading of the implant 10 into the mounting flange 20.

Figure 2:
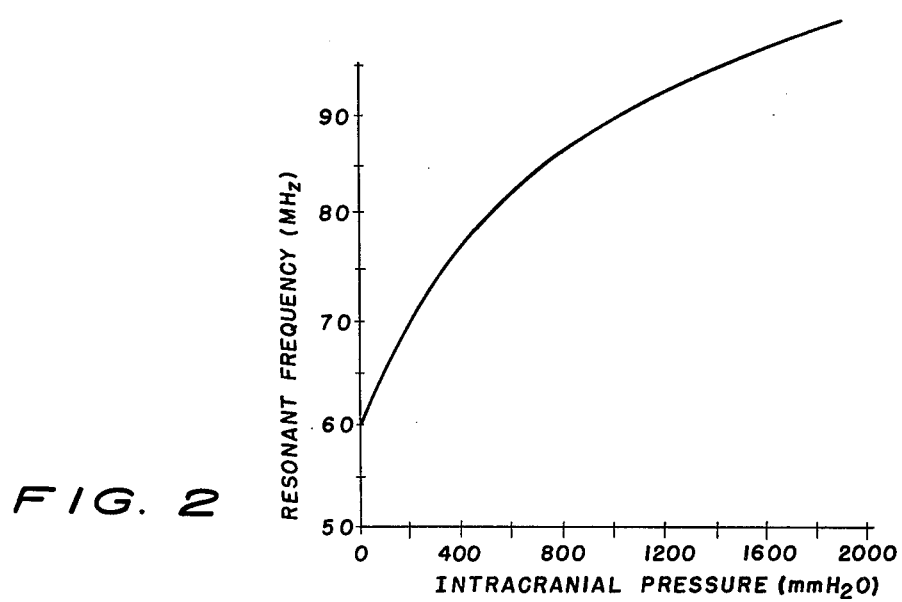
FIG. 2 is a graph illustrating the resonant frequency response of a typical transducer embodying the principles of the present invention versus sensed intracranial pressure.

It should be apparent that increases in pressure within the dura sensed upon the flexible membrane 42 are translated into contraction of the bellows 56 and visa versa. As a result, when cranial pressure is close to one atmosphere, the fixed capacitance plate 52 and the movable capacitance plate 58 are in perigee and approach apogee as pressure increases. The result of this relationship on the inductor-capacitor circuit is graphically illustrated in FIG. 2 by test data taken from testing of an intracranial pressure monitoring implant 10 constructed according to the principles of the present invention. An increase in intracranial pressure will cause contraction of the bellows 56 thereby reducing the capacitance in the inductor-capacitor circuit. This by definition leads to an increase in the resonant frequency of the resonant circuit. Since the capacitance developed between the fixed capacitance plate 52 and the movable capacitance plate 58 is an inverse function of spacing, given the natural relationship between capacitance and resonant frequency, the present invention shows the most sensitivity; i.e., the greatest frequency shift at pressures close to normal cranial pressure.

Since maximum capacitance exists in the resonant circuit at pressures closest to normal cranial pressure the ratio between capacitance in the resonant circuit and stray capacitance attributable to the electrically conductive body fluids in which the implant is placed is optimized so that resonant frequency shift of the resonant circuit upon implantation of the pressure monitor implant 10 is minimized and becomes negligible. Resultantly, a distinct advantage is presented over implants which are at minimum capacitance when implanted and therefore experience frequency shifts upon implantation.

Operation of the intracranial pressure monitoring implant 10 can be further characterized by the following mathematical relationships, the pressure $P_o$ external of the implant 10 being related to the pressure $P_1$ by the following:

$$P_o = P_1 + k/A(X_o - X)$$

where:
- $k$ = the spring constant of the bellows 56;
- $A$ = the cross-sectional area of the movable capacitance plate 58;
- $X_o$ = the neutral i.e. unstressed position of the bellows 56; and
- $X$ = the stressed position of the bellows.

The internal pressure $P_1$ can be expressed in terms of temperature as follows:

$$P_1 = P_C/T_C T$$

where $P_C$ and $T_C$ are respectively the closure pressure and temperature at the time the implant 10 is assembled. The ideal value for these last two parameters are 10,336 millimeters of $H_2O$ (760 millimeters of $H_g$) and 558° R (body temperature, absolute). Hence, the temperature sensitivity of the implant 10 is 18.5 millimeters $H_2O/F°$ and the formula giving the pressure correction $P_T$ for body temperature $T_\beta$ is;

$$P_T = 18.5(T_\beta - 98.6)$$

The distance X in milli/inches of the surface of the movable capacitance plate 58 of the bellows 56 from the fixed capacitance plate 52 can be given in terms of the resonant RF frequency $\omega$ of the resonant circuit as follows:

$$X = (\omega^2 LK) \div (1 - \omega^2 LC_p)$$

where:
- L = inductance ($1.4 \times 10^{31\ 6}$ Henries);
- K = a dielectric constant (4.039) and
- $C_p$ = stray capacitance in Farads Since the implant 10 essentially acts as a small borometer and is thereby responsive to absolute atmospheric pressure, correction for barometric pressure can be included in the monitor or corrections can be made to the pressures indicated by the monitor taking into consideration variation of barometric pressure.

Figure 6:
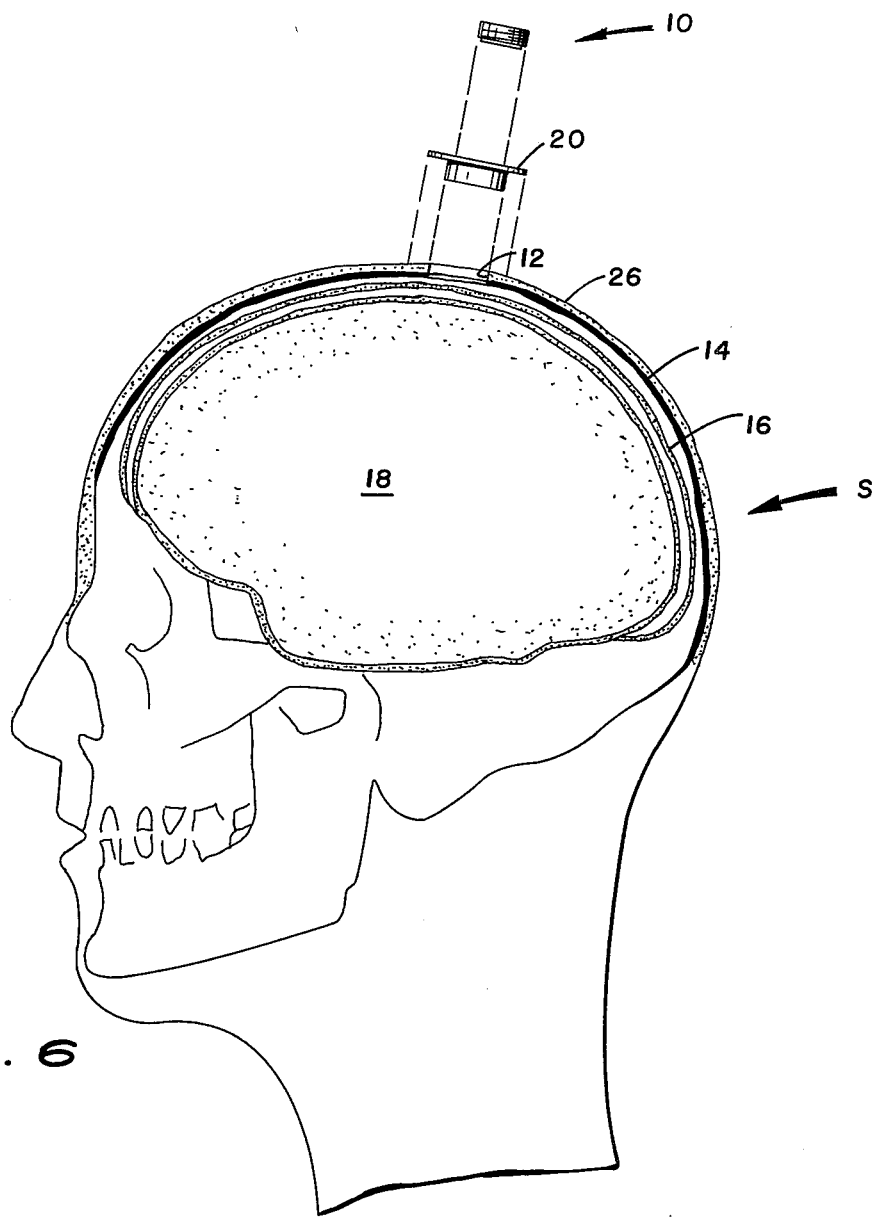
FIG. 6 is a schematic representation illustrating the manner in which the present invention is mounted in the cranium of a subject.
Figure 7:
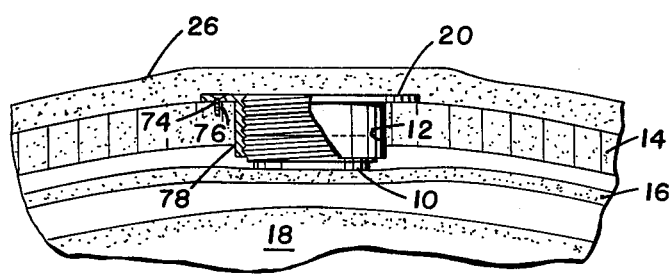
FIG. 7 is a detailed fragmentary elevation in partial section of the preferred embodiment after it has been implanted.

One manner in which the intracranial pressure monitor implant 10 may be placed within the skull 14 of a subject S is illustrated in detail in FIGS. 6 and 7. The mounting flange 20, as also shown in FIG. 3, is positioned within the burr hole 12. The burr hole 12 is made in the skull 14 by known techniques. For instance, an air driven trephine or brace trephine is used to make the hole 12, the cavity of the skull 14 being trimmed with a curette to expose a circular area of dura. Bone wax is used to reduce bleeding from the walls of the burr hole 12 and a bipolar coagulator could be used to stop any bleeding which may exist on the surface of the exposed dura 16. Once the burr hole 12 is formed, the mounting flange 20 may be attached to the skull 14. The flange 20 provides a pair of apertures 74 which accommodate a pair of skull screw 76 or sutures, not shown, to permit affixment of the flange 20 to the periosteum or bone. If the periosteum is not available, the galea tissue is turned over the flange 20 as a flap and is secured with interrupted sutures. The scalp margins are approximated for subsequent wound closure. The mounting flange 20 provides a neck 78 into which the housing 28 may be threaded. Typically, the implant 10 is threaded into the neck 78 until the lowermost surface of the cover 36, the membrane 42, contacts the dura matter 16. The housing 28 is not screwed down far enough to deflect the dura 16 substantially but rather is positioned so that contact is established between the same and the flexible membrane 42. It should be apparent to one skilled in the art that other structures may be employed to position the intracranial pressure monitoring implant 10 of the present invention within the skull of a subject.

The foregoing description pertains to an intracranial pressure monitoring implant having a resonant circuit wherein an inductor of a fixed value and a capacitor of a variable value are employed. It should be apparent to those skilled in the art that a capacitor of a fixed value and an inductor of a variable value can comprise a resonant circuit substitutable for the configuration described without departing from the scope of the invention.

It should be understood that various changes in the details, materials, arrangements of parts and operational conditions which have been herein described and illustrated in order to explain the nature of the invention may be made by those skilled in the art within the principles and scope of the invention.

Having thus set forth the nature of the invention what is claimed is:

1. An apparatus for sensing pressure within a cavity in the body of a living entity and for implantation within said body comprising:
   inductor-capacitor resonant circuit means;
   pressure responsive means for responding to said pressure disposed in said cavity; and
   means for increasing the resonant frequency of said resonant circuit means in response to an increase in said pressure as sensed by said pressure responsive means and for decreasing said resonant frequency of said resonant circuit means in response to a decrease in said pressure as sensed by said pressure responsive means, said means for increasing and decreasing said resonant frequency comprising deformable means for acting upon said inductor-capacitor resonant circuit means to vary the frequency thereof in response to deformation of the configuration of said deformable means, said deformable means sealing therein a predetermined quantity of a compressible medium, said deformable means thereby serving as a reference pressure source.

2. An apparatus in accordance with claim 1, wherein said pressure responsive means comprises means moveable in response to said pressure within said cavity, the movement of said moveable means causing said means for increasing and decreasing said resonant frequency to shift said resonant frequency by varying the reactance of at least one of the reactive components of said inductor-capacitor resonant circuit means.

3. An apparatus in accordance with claim 2, further comprising:
a rigid housing of a non-porous and electrically non-conductive material for total implantation in said cavity, said housing forming a chamber, said inductor-capacitor circuit being disposed within said chamber;
said moveable means being carried on said housing and communicating said pressure to the interior of said chamber;
said means for increasing and descreasing said resonant frequency further comprising
said deformable means being disposed within said chamber, and
a predetermined mass of fluid disposed within said chamber, said fluid permitting said pressure communicated to the interior of said housing by said pressure responsive means to deform the configuration of said deformable means.

4. An apparatus in accordance with claim 3, wherein said moveable means comprises an impervious flexible membrane carried by said housing.

5. An apparatus in accordance with claim 4, wherein said deformable means comprises a sealed bellows, said predetermined quantity of a compressible medium being disposed therein.

6. An apparatus in accordance with claim 5, wherein said inductor-capacitor resonant circuit means comprises an inductor of a fixed inductance and a variable capacitor, said means for increasing and decreasing said resonant frequency comprising means for varying the capacitance of said variable capacitor.

7. An apparatus in accordance with claim 6, wherein said bellows has an electrically conductive surface movable relative to a fixed location within said chamber, a fixed electrically conductive surface being disposed at said fixed location, said fixed and movable electrically conductive surfaces forming said variable capacitor.

8. An apparatus in accordance with claim 7, wherein said bellows is formed of an electrically conductive material, one end of said bellows being fixed in position relative to said fixed location, the other end of said bellows being movable relative to said fixed location and providing said movable electrically conductive surface, said fixed and movable electrically conductive surfaces being planar and substantially parallel, said inductor being operably electrically coupled between said fixed electrically conductive surface and said bellows to form said resonant circuit means.

9. An apparatus in accordance with claim 8, further comprising a unitary rigid spacer, said spacer comprising a unitary wall having first and second opposed edges lying, respectively, in first and second substantially parallel planes, said wall forming a substantially straight support between said edges, said one end of said bellows being fixedly secured to said first edges of said wall, said fixed electrically conductive surface being fixedly secured to said second edges of said wall, said unitary wall fixing the distance between said one end of said bellows and said fixed electrically conductive surface independent of said housing.

10. An apparatus in accordance with claim 9, wherein said unitary wall is tubular and forms a chamber therein, said other end of said bellows being moveable within said chamber formed by said unitary wall.

11. An apparatus in accordance with claim 10, wherein said fixed electrically conductive surface has a plurality of apertures disposed therethrough, said aperture for permitting the passage of said fluid into and out of said longitudinal chamber.

12. An apparatus in accordance with claim 10, wherein said rigid spacer is constructed of quartz glass.

13. An apparatus in accordance with claim 5 wherein said mass of fluid comprises silicone oil and said compressible medium comprises nitrogen gas.

14. In an apparatus for sensing pressure within a cavity in the body of a living entity having a housing for location within said cavity and a fixed inductor-variable capacitor circuit means whose resonant frequency shifts with changes in said pressure, said variable capacitor providing mechanically arrangeable means having a fixed portion and a moveable electrically conductive surface, said variable capacitor also providing a fixed electrically conductive surface, the improvement comprising, unitary rigid spacer means disposed between said fixed portion of said mechanically arrangeable means and said fixed electrically conductive surface, said spacer means comprising a unitary wall having a first and a second opposed edge lying, respectively, in first and second substantially parallel planes, said wall forming a substantially straight rigid support between said edges, said mechanically arrangeable means being fixedly secured to said first edge, said fixed electrically conductive surface being fixedly secured to said second edge, said unitary wall fixing the distance between said fixed portion of said mechanically arrangeable means and said fixed electrically conductive surface independent of said housing.

15. An apparatus in accordance with claim 14, wherein said unitary wall comprises a tubular element forming a chamber.

16. An apparatus in accordance with claim 15, wherein said mechanically arrangeable means comprises a bellows, said fixed portion being a fixed end of said bellows which is fixedly secured to one end of said tubular element, said movable portion being a movable end of said bellows which is movable within said longitudinal chamber, said movable electrically conductive surface being connected to said movable end of said bellows.

17. An apparatus in accordance with claim 16, wherein said bellows is constructed of an electrically conductive material, said movable electrically conductive surface being integral therewith.

18. An apparatus in accordance with claim 15, wherein said tubular element is constructed of quartz glass.

* * * * *

UNITED STATES PATENT AND TRADEMARK OFFICE
CERTIFICATE OF CORRECTION

PATENT NO. : 4,265,252
DATED : May 5, 1981
INVENTOR(S) : John G. Chubbuck and James T. Turner It is certified that error appears in the above—identified patent and that said Letters Patent is hereby corrected as shown below:

Column 5, line 43, delete "45" and replace therefor -- 54 --.

Column 7, line 14, delete "$P_1$" and replace therefor -- $P_\iota$ --.

Column 7, line 16, delete "$P_o = P_1 + k/A(X_o - X)$" and replace therefor

-- $P_o = P_\iota + \frac{k}{A}(X_o - X)$ --.

Column 7, line 26, delete "$P_1$" and replace therefor -- $P_\iota$ --.

Column 7, line 28, delete "$P_1 = P_C/T_C T$" and replace therefor

-- $P_\iota = \frac{P_C}{T_C} T$ --.

Column 7, line 49, delete "(1.4x10$^{316}$ Henries);" and replace therefor -- (1.4 x 10$^{-6}$ Henries); --.

Signed and Sealed this

Twenty-seventh Day of April 1982

[SEAL]

Attest:

GERALD J. MOSSINGHOFF

Attesting Officer     Commissioner of Patents and Trademarks